(12) United States Patent
Kim et al.

(10) Patent No.: US 11,147,693 B2
(45) Date of Patent: Oct. 19, 2021

(54) ARTIFICIAL FOOT HAVING ROTATABLE TOE PART

(71) Applicant: KOREA WORKERS' COMPENSATION & WELFARE SERVICE, Seoul (KR)

(72) Inventors: Hyun Cheol Kim, Incheon (KR); Suk Min Lee, Bucheon-si (KR); Jeom Sik Song, Incheon (KR); Jei Cheong Ryu, Seoul (KR); Chil Yong Kwon, Bucheon-si (KR); Hyeon Seok Cho, Incheon (KR)

(73) Assignee: Korea Workers' Compensation & Welfare Service, Seoul (KR)

( * ) Notice: Subject to any disclaimer, the term of this patent is extended or adjusted under 35 U.S.C. 154(b) by 0 days.

(21) Appl. No.: 16/640,287

(22) PCT Filed: Aug. 31, 2017

(86) PCT No.: PCT/KR2017/009551
§ 371 (c)(1),
(2) Date: Feb. 19, 2020

(87) PCT Pub. No.: WO2019/045145
PCT Pub. Date: Mar. 7, 2019

(65) Prior Publication Data
US 2020/0360158 A1 Nov. 19, 2020

(30) Foreign Application Priority Data
Aug. 30, 2017 (KR) .................. 10-2017-0110310

(51) Int. Cl.
*A61F 2/66* (2006.01)
*A61F 2/50* (2006.01)

(52) U.S. Cl.
CPC .............. *A61F 2/66* (2013.01); *A61F 2/6607* (2013.01); *A61F 2002/5038* (2013.01);
(Continued)

(58) Field of Classification Search
CPC .. A61F 2/66; A61F 2/6607; A61F 2002/6621; A61F 2002/6657;
(Continued)

(56) References Cited

U.S. PATENT DOCUMENTS

| 6,129,766 A | 10/2000 | Johnson et al. |
| 8,007,544 B2 * | 8/2011 | Jonsson ..................... A61F 2/76 623/38 |

(Continued)

FOREIGN PATENT DOCUMENTS

| JP | 2016-514505 A | 5/2016 |
| JP | 2017-514569 A | 6/2017 |

(Continued)

*Primary Examiner* — Bruce E Snow
(74) *Attorney, Agent, or Firm* — Rabin & Berdo, P.C.

(57) ABSTRACT

The present invention relates to an artificial foot including a foot body part, a toe part rotatably disposed at a first end of the foot body part, a toe joint connecting the foot body part and the toe part to each other, and an adapter disposed on a top of a second end of the foot body part. According to the artificial foot, since the toes of the artificial foot rotate when a wearer walks, when the artificial toes come in contact with the ground, energy is stored due to the load by the weight and the toes kick off the ground as much as the elastic energy accumulated by the spring, so the toe members of the artificial foot do not drag on the ground. Accordingly, the wearer does not need to lift up the hip joints, so the wearer can walk similar to normal walking.

15 Claims, 7 Drawing Sheets

(52) U.S. Cl.
CPC ................ *A61F 2002/6614* (2013.01); *A61F 2002/6621* (2013.01); *A61F 2002/6642* (2013.01); *A61F 2002/6657* (2013.01)

(58) Field of Classification Search
CPC ...... A61F 2002/6607; A61F 2002/6614; A61F 2002/6642
See application file for complete search history.

(56) References Cited

U.S. PATENT DOCUMENTS 8,764,850 B2 * 7/2014 Hansen ..................... A61F 2/70
623/47
10,292,840 B2 * 5/2019 Schlafly ................ A61F 2/6607

FOREIGN PATENT DOCUMENTS

| | | |
|---|---|---|
| KR | 10-0401458 B1 | 12/2003 |
| KR | 10-2016-0038244 A | 4/2016 |
| KR | 10-1763479 B1 | 8/2017 |

* cited by examiner

ARTIFICIAL FOOT HAVING ROTATABLE TOE PART

TECHNICAL FIELD

The present invention relates to an artificial foot having a rotatable toe part and, more particularly, to an artificial foot that enables a user wearing artificial limb to almost normally walk because a toe part thereof can be rotated by toe joints.

BACKGROUND ART

An artificial limb, which is artificially manufactured to be suitable for partial deficiency of a foot in terms of external shape and function, generally includes a lower artificial limb that is so-called an artificial leg and is composed of an artificial foot, a pipe adapter, a through-pipe, a socket adapter, and a socket. A socket liner is coupled to an amputated portion and is connected to an artificial limb having a socket. A user wearing an artificial limb has to walk in the same way as people without disability in order to easily and conveniently walk. However, unless an artificial limb provides functionally the same joints as those of people without disability, a user wearing the artificial limb never walk similar to normal walking.

FIG. 1 is an image view of an artificial foot according to the related art. As shown in FIG. 1, an artificial foot of the related art has a structure including one foot-shaped composite member (keel member) without toe joints, thereby enabling a wearer to walk using elasticity by bending when load is applied by the weight of the wearer. Accordingly, there is no device that can adjust the angles of toe joints at a taking-off timing of toes at which toes takes of the ground, so there is a defect that stable walking is not secured and the wearer feels inconvenience when walking. In particular, it is difficult to keep the balance of the body on the ground with an uneven surface.

Further, it is impossible to freely control the ankle joint, and there is a limitation in the entire daily life that requires controlling the ankle joint such as walking on a slope or wearing/not wearing a heeled shoe.

DISCLOSURE

Technical Problem

The present invention has been made in an effort to solve the problems in the related art and an object of the present invention is to provide an artificial foot that enables a wearer to walk similar to normal walking by connecting an artificial foot body and artificial toes through a toe connection pin to that they can rotate and by connecting an upper adapter to the upper portion of the artificial foot body through an adapter pin so that the ankle can rotate.

Technical Solution

In order to achieve the objects, an aspect of the present invention relates to an artificial foot including: a foot body part; a toe part rotatably disposed at a first end of the foot body part; a toe joint connecting the foot body part and the toe part to each other; and an adapter disposed on a top of a second end of the foot body part.

In the artificial foot according to an embodiment of the present invention, the toe joint may include a toe connection member and a first elastic member, the first elastic member may be disposed between the toe part and the foot body part and elastically supports the toe part, and the toe connection member may connect the toe part and the foot body part to each other such that the toe part can rotate.

Further, the toe part may pivot on the toe connection member.

Further, a rotation angle ($\theta$) of the pivoting $\theta$ may be $0 \leq \theta \leq 90°$.

Further, the toe connection member may be a hinge pin.

Further, the first elastic member may be a torsion spring.

Further, the foot body part may include a foot body, a second elastic member accommodation groove, and a cushion rubber.

Further, the toe part may include toe members and a toe connection member connection hole.

Further, the toe joint may include a toe connection member and a first elastic member.

Further, the adapter may include an adapter body, an adapter connection member connection hole, and an artificial limb-fastening pyramid.

Further, the artificial foot may further include an ankle joint.

Further, the ankle joint may include an adaptor connection member and a second elastic member.

Further, the ankle joint may be disposed between the foot body part and the adapter and rotatably connects the adapter to the foot body part.

Further, the second elastic member may be made of elastic rubber.

Further, the second elastic member may be disposed in a second elastic member accommodation groove formed in the foot body part.

Further, the second elastic member and the second elastic member accommodation groove may be formed in any one of cylindrical, elliptical cylindrical, and polygonal cylindrical shapes; a size of a cross-section cut perpendicular to a central axis of the second elastic member may be smaller than a size of a cross-section cut perpendicular to a central axis of the second elastic member accommodation groove, a height ($h_1$) of the second elastic member is larger than a height ($h_2$) of the second elastic member accommodation groove ($h_1 > h_2$); and when the second elastic member maximally deforms, the second elastic member may fill the entire second elastic member accommodation groove, and the height ($h_1$) of the second elastic member and the height ($h_2$) of the second elastic member accommodation groove may be 0 mm $< h_1 - h_2 \leq 5$ mm.

Further, the second elastic member and the second elastic member accommodation groove may be formed in cylindrical shapes; a diameter ($d_1$) of a cross-section cut perpendicular to a central axis of the second elastic member may be smaller than a diameter ($d_2$) of a cross-section cut perpendicular to a central axis of the second elastic member accommodation groove a ($d_1 < d_2$), a height ($h_1$) of the second elastic member is be larger than a height ($h_2$) of the second elastic member accommodation groove ($h_1 > h_2$); and when the second elastic member maximally deforms, the second elastic member may fill the entire second elastic member accommodation groove, and the height ($h_1$) of the second elastic member and the height ($h_2$) of the second elastic member accommodation groove may be 0 mm $< h_1 - h_2 \leq 5$ mm.

Further, the adapter connection member may connect the adapter and the foot body part such that the adapter can rotate, and the second elastic member may be disposed between the adapter and the foot body part and elastically supports the adapter.

Further, the adapter may pivot on the adapter connection member.

Further, the adapter connection member may be a hinge pin.

Further, the artificial foot further includes a cushion part on a side of the lower portion of the foot body part.

Advantageous Effects

According to the artificial foot of the present invention, since the toes of the artificial foot rotate when a wearer walks, when the artificial toes come in contact with the ground, energy is stored due to the load by the weight and the toes kick off the ground as much as the elastic energy accumulated by the spring, so the toe members of the artificial foot do not drag on the ground. Accordingly, the wearer does not need to lift up the hip joints, so the wearer can walk similar to normal walking.

Further, since the ankle joint and the toes of artificial foot rotate and kick off the ground using the energy obtained by the weight of the wearer on a slope, so there is an effect that it is possible to minimize dragging.

BEST MODE

Figure 1:
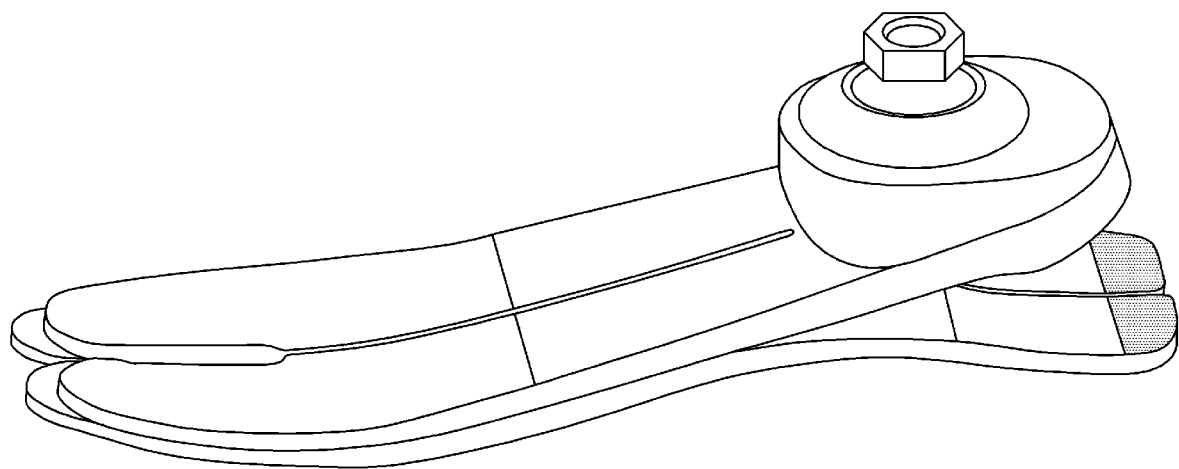
FIG. 1 is an image view of an artificial foot according to the related art.

The present invention may be modified in various ways and implemented by various exemplary embodiments, so that specific exemplary embodiments are shown in the drawings and will be described in detail herein. However, it is to be understood that the present invention is not limited to the specific exemplary embodiments, but includes all modifications, equivalents, and substitutions included in the spirit and the scope of the present invention. In describing the present invention, detailed descriptions of well-known technologies will be omitted so as not to obscure the description of the present invention with unnecessary detail.

Terms including ordinal numbers such as "first", "second", etc., may be used to describe various components, but the components are not to be construed as being limited to the terms. The terms are used only to distinguish one component from another component. For example, the "first" component may be named the "second" component, and vice versa, without departing from the scope of the present invention.

Further, when a component is stated as "being on another component", "being formed on another component", or "being stacked on another component", the component may be directly attached to or stacked on the entire or a portion of the surface of another component, but another component may further exist therebetween.

Singular forms are intended to include plural forms unless the context clearly indicates otherwise. It will be further understood that the terms "comprises" or "have" used in this specification, specify the presence of stated features, steps, operations, components, parts, or a combination thereof, but do not preclude the presence or addition of one or more other features, numerals, steps, operations, components, parts, or a combination thereof.

Hereafter, artificial foot of the present invention is described in detail. However, this is provided only an example and the present invention is not limited thereto and is defined only by the following claims.

Figure 2:
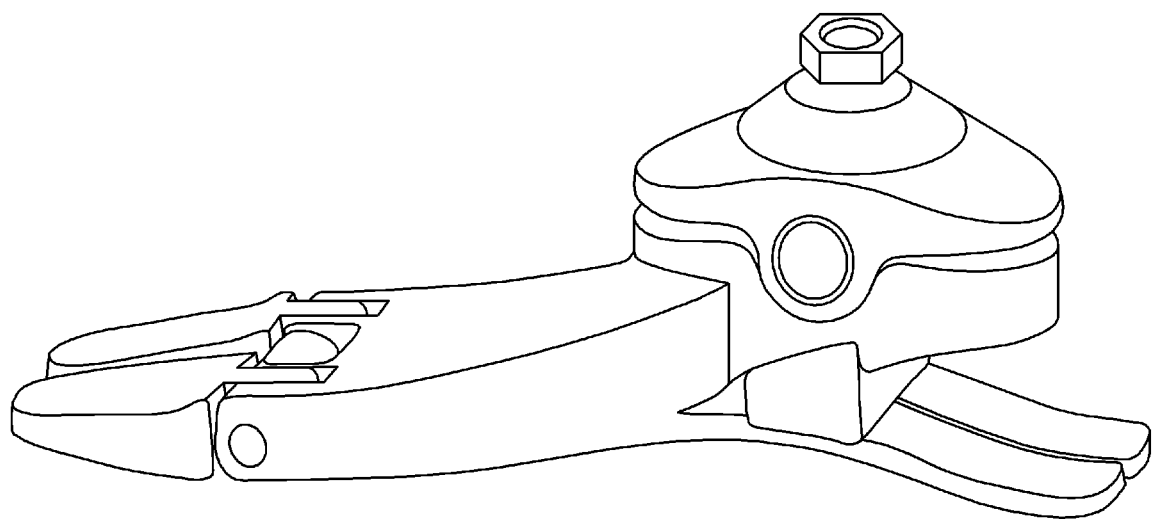
FIG. 2 is an image view of an artificial foot according to the present invention.
Figure 3:
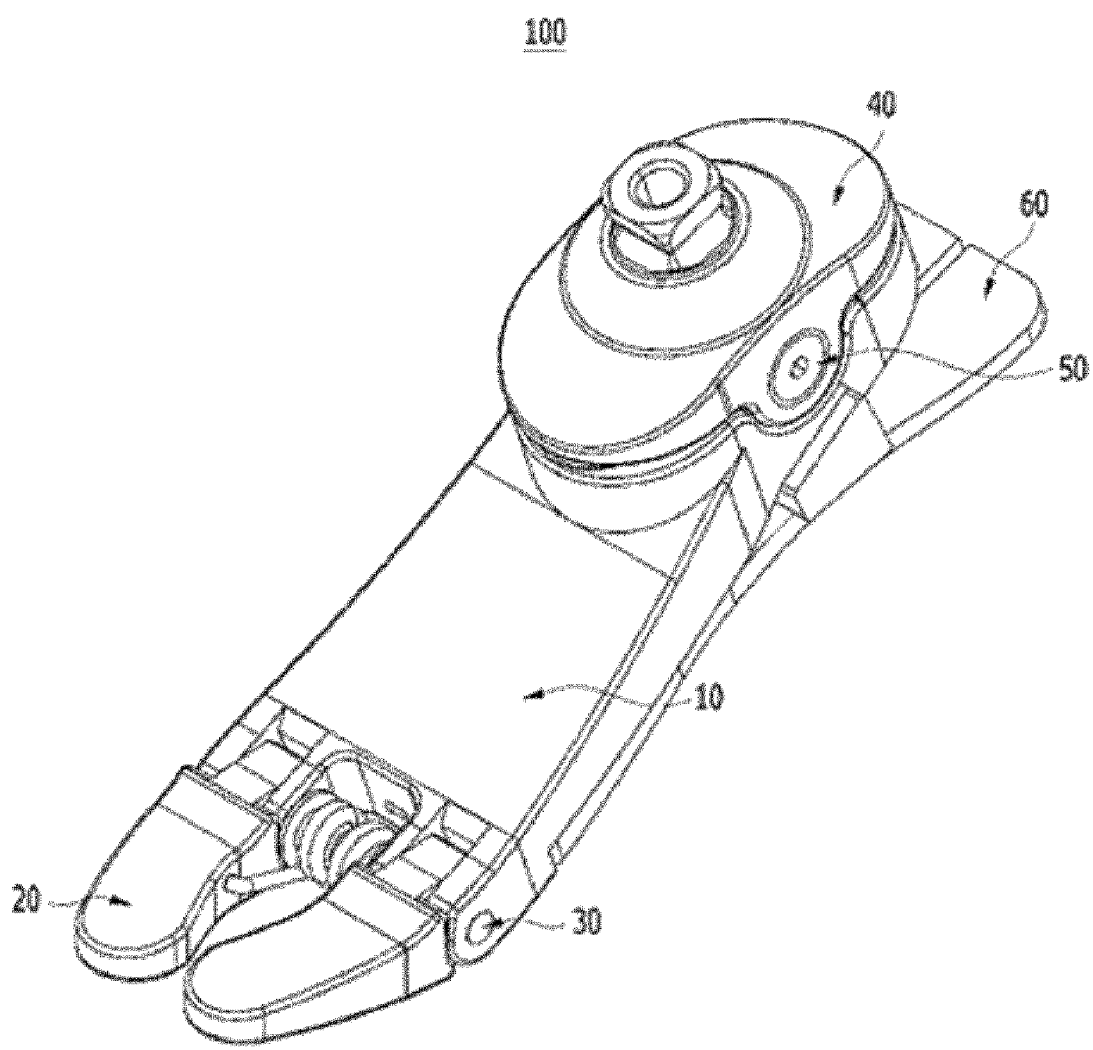
FIG. 3 is a perspective view of the artificial foot according to the present invention.
Figure 4:
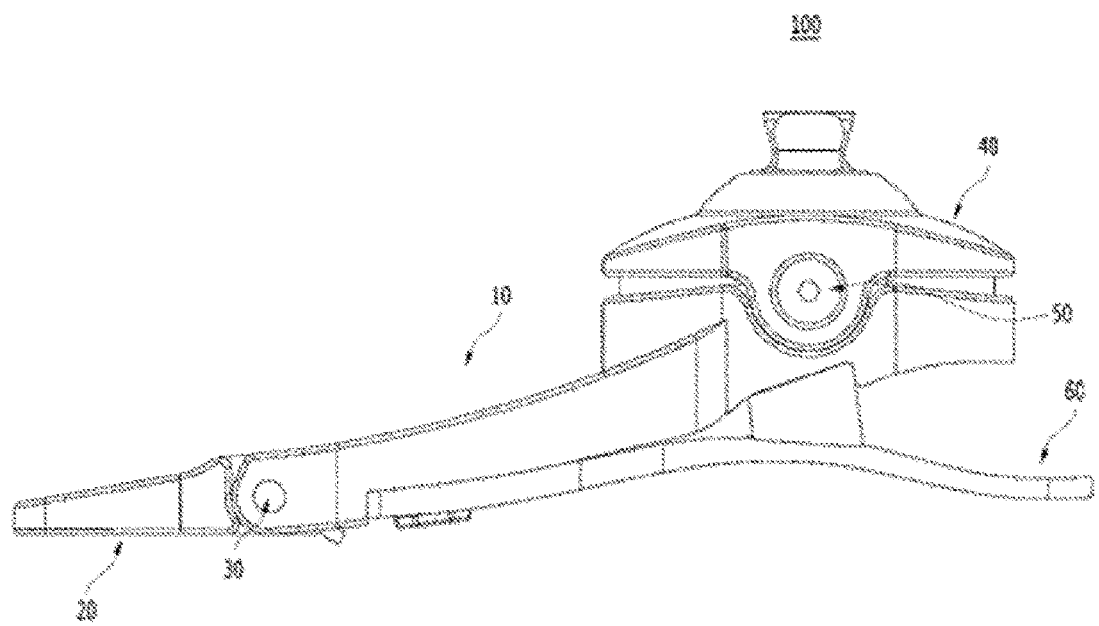
FIG. 4 is a side of the artificial foot according to FIG. 3.
Figure 5:
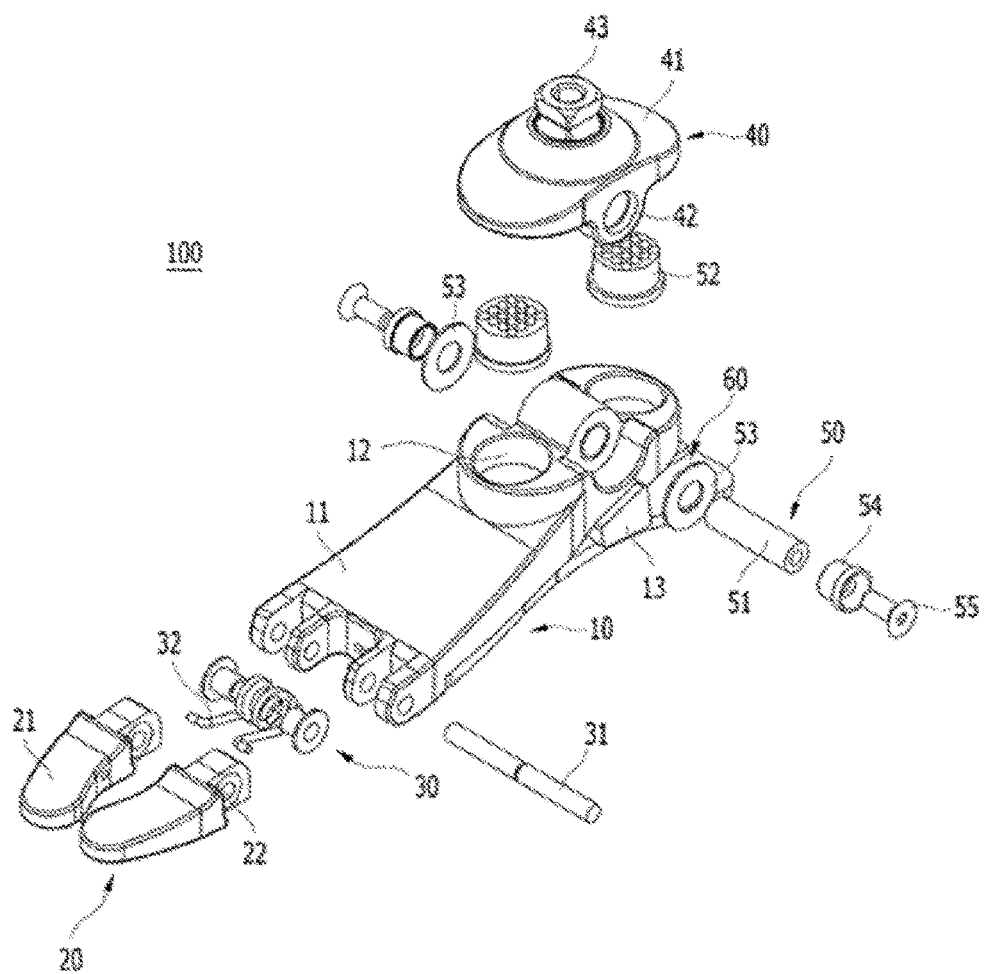
FIG. 5 is an exploded perspective view of the artificial foot according to FIG. 3.

FIG. 2 is an image view of an artificial foot according to the present invention, FIG. 3 is a perspective view of the artificial foot according to the present invention, FIG. 4 is a side of the artificial foot according to FIG. 3, and FIG. 5 is an exploded perspective view of the artificial foot according to FIG. 3.

Referring to FIGS. 2 to 5, an artificial foot 100 according to the present invention includes a foot body part 10, a toe part 20 rotatably disposed at a first end of the foot body part 10, a toe joint 30 connecting the foot body part 10 and the toe part 20, and an adapter 40 disposed on the top of a second end of the foot body part 10.

The foot body part 10 includes a foot body 11, a second elastic member accommodation groove 12, and a cushion rubber 13. The foot body part 10, which is designed to be connected at a side to an artificial limb that patients with their lower leg or thigh cut wear to be able to support the weight of the wearers, is configured to be able to support a wearer walking and moving the center of his/her body in a stance phase. In detail, the foot body 11 has a predetermined area to support a wearer so that the wearer can stand up, and the adapter 40 that can be connected to an artificial limb is disposed at a side on the top thereof. The foot body 11 is not limited in shape as long as it can stably support a wearer, but may have a predetermined length to be similar to the shapes of the feet of common people. The second elastic member accommodation groove 12 and the cushion rubber 13 will be described below.

In the present invention, the toe part 20 includes toe members 21. The toe members 21 are coupled to an end of the foot body part 10 to be rotatable by a toe joint 30 and are separated into two or three pieces to be able to distribute and support the weight of a wearer on an irregular surface such as an uneven surface or a slope, thereby being able to enable stable walking. Although two toe members 21 are exemplified in an embodiment of the present invention, it is only for improving convenience for a user and three or more toe members 21 may be selectively provided. A toe connection member connection hole 22 is formed at ends of the toe members 21 and a toe connection member 31 of the toe joint 30 is fitted in the connection holes 22.

According to the present invention, the toe connection member 31 may be a hinge pin. Accordingly, the toe part 20 pivots up and down on the toe connection members 31 with respect to the foot body part 10. The rotation angle ($\theta$) of the pivot movement may be performed in the range of $0° \leq \theta \leq 90°$, preferably $0° \leq \theta \leq 60°$, and more preferably $0° \leq \theta \leq 30°$.

In the present invention, the toe joint 30 includes the toe connection member 31 and a first elastic member 32. The toe connection member 31 connects the toe part 20 and the foot body part 10 such that the toe part 30 can rotate with respect to the foot body 11. The first elastic member 32 is positioned between the toe part 20 and the foot body part 10, thereby elastically supporting the toe part 20. The first elastic member 32 may be a torsion spring.

Referring to FIG. 19.3 and the contents on PP416-418 in "Gait Analysis, Normal and Pathological Function" by J. Perry et. al, which is a work about analysis of ground reaction force for each walking step of human, the ground reaction force at the latter stage of a swing phase (a period in which the sole of a foot comes in contact with the ground) while a person walks is about 23% of the weight. That is, it can be seen that if the weight is 100 kg, force of about 23 kg is required at a toe joint.

Figure 6:
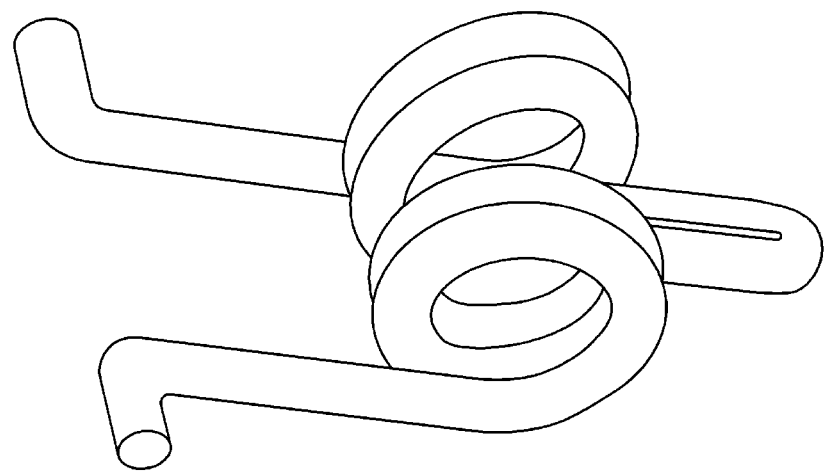
FIG. 6 is a photograph of a torsion spring that is used in the present invention.

FIG. 6 is a photograph of the torsion spring 32 that is used in the present invention. The torsion spring 32 of the present invention may be manufactured such that the elasticity charges over 23% of weight on the basis of the above description. In an embodiment of the present invention, the torsion spring 32 is a pair torsion spring wound left and right and provides elasticity to the toe members 21.

Since the artificial foot 100 according to the present invention, as described above, includes the toe joint 30, when a wearer walks, the toe part 20 of the artificial foot 100 rotates. Accordingly, when the toe members 21 come in contact with the ground, energy is stored due to the load by the weight and the toe members 21 kick off the ground as much as the elastic energy accumulated by the spring 32, so the toe members 21 of the artificial foot do not drag on the ground. Accordingly, the wearer does not need to lift up the hip joints, so the wearer can walk similar to normal walking.

The artificial foot 100 according to an embodiment of the present invention may further include an ankle joint 50 disposed between the foot body part 10 and the adapter 40 and rotatably connecting the adapter 40 to the foot body part 10.

The adapter 40, which is a part to which an artificial limb is connected, includes an adapter body 41, an adapter connection member connection hole 42, and an artificial limb-fastening pyramid 43. The ankle joint 50 connects the adapter 40 and the foot body part 10 to each other such that the adapter 40 can rotate with respect to the foot body part 10. The ankle joint 50 includes an adapter connection member 51, a second elastic member 52, a washer 53, a shaft-fixing guide 54, and a bolt 55. The adapter connection member 51 is fixed in the shaft-fixing guide 54 and fitted in the adapter connection member connection hole 42. The adapter connection member 51 may be a hinge pin. Accordingly, the adapter 40 pivots forward and backward on the adapter connection member 51 with respect to the foot body part 10.

According to the present invention, a second elastic member accommodation groove 12 is formed at a side on the top of the foot body 11. The second elastic member 52 is positioned in the second elastic member accommodation groove 12. The second elastic member 52 may be an elastic rubber. Accordingly, the second elastic member 52 elastically supports the adapter 40 to the foot body part 10. The amount of deformation of the second elastic member 52 may be limited in accordance with the size of the second elastic member accommodation groove 12.

Figure 7:
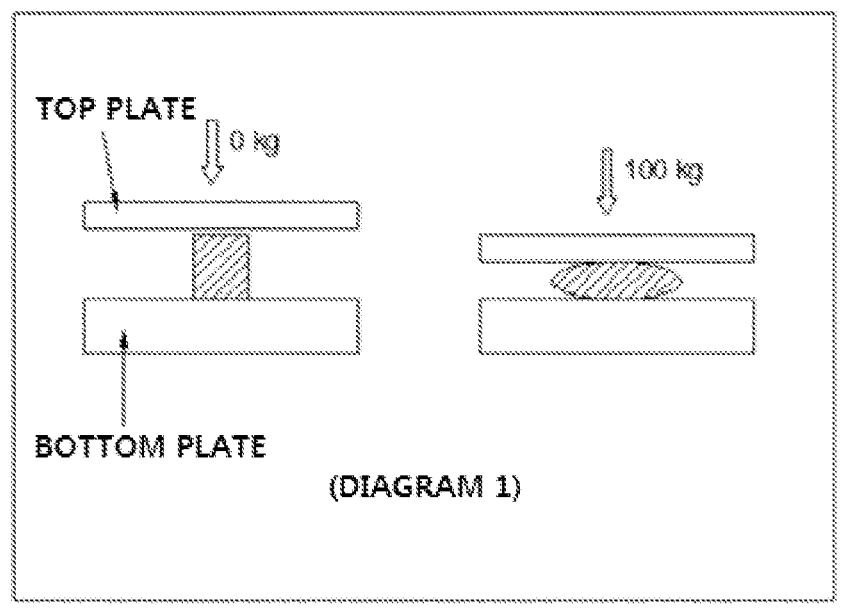
FIG. 7 is a schematic view illustrating states before and after deformation of an elastic rubber fitted between a top plate and a bottom plate due to a load.

The function of the second elastic member 52 according to the present invention is described hereafter. FIG. 7 is a schematic view illustrating states before and after deformation of a general elastic rubber fitted between a top plate and a bottom plate due to a load. As shown in FIG. 7, when external force is applied to rubber, the rubber deforms as much as the magnitude of the external force. Accordingly, when a load such as repeated fatigue is continuously applied, the physical properties of the rubber change, and as a result, the intrinsic property is lost.

Figure 8:
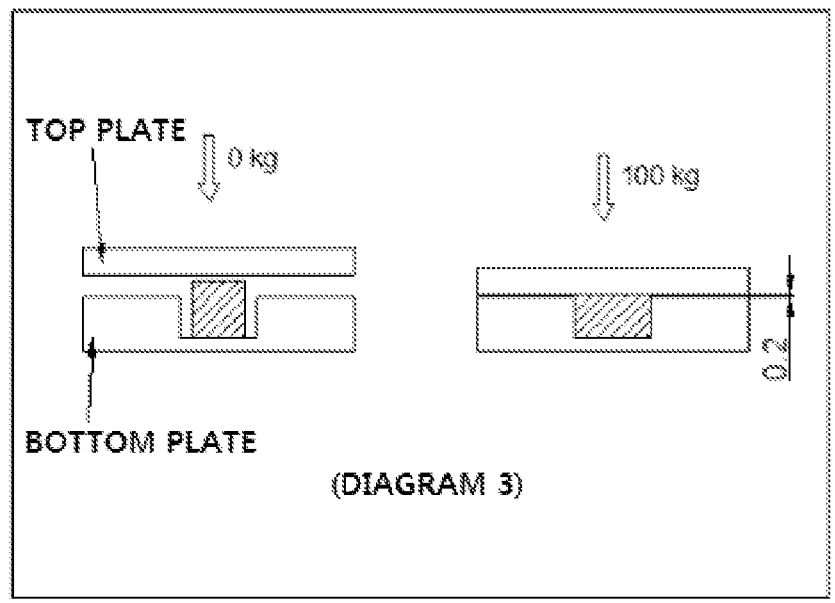
FIG. 8 is a schematic view illustrating the function of the elastic member according to the present invention.

Meanwhile, FIG. 8 is a schematic view illustrating the function of the elastic member according to the present invention. Referring to FIG. 8, an elastic member made of rubber is fitted between a top plate and a groove of a bottom plate and is deformed by a load. That is, when an external force is applied to the elastic member made of rubber, the elastic member is deformed as much as the magnitude of the external force. However, the area of the groove of the bottom plate is larger than the area of the rubber in FIG. 8, so when an external force is applied, the rubber deforms, but does not deform more than the size designed in accordance with the volume. Accordingly, even if a load such as repeated fatigue is continuously applied, the physical properties of the rubber do not easily change and the intrinsic physical properties can be maintained for a long period of time.

In the artificial foot 100 according to an embodiment of the present invention, the second elastic member 52 and the second elastic member accommodation groove 12 may be formed in any one of cylindrical, elliptical cylindrical, and polygonal cylindrical shapes. In this case, the size of the cross-section cut perpendicular to the central axis of the second elastic member 52 may be smaller than the size of the cross-section cut perpendicular to the central axis of the second elastic member accommodation groove 12, the height ($h_1$) of the second elastic member 52 may be larger than the height ($h_2$) of the second elastic member accommodation groove ($h_1 > h_2$), and when the second elastic member 52 maximally deforms, the second elastic member 52 may fill the entire second elastic member accommodation groove 12, and the height ($h_1$) of the second elastic member 52 and the height ($h_2$) of the second elastic member accommodation groove 12 may be 0 mm $< h_1 - h_2 \leq$ 5 mm.

Further, the second elastic member 52 and the second elastic member accommodation groove 12 may be formed in cylindrical shapes. In this case, the diameter ($d_1$) of a cross-section cut perpendicular to the central axis of the second elastic member 52 may be smaller than the diameter ($d_2$) of a cross-section cut perpendicular to the central axis of the second elastic member accommodation groove 12 ($d_1 < d_2$), the height ($h_1$) of the second elastic member 52 may be larger than the height ($h_2$) of the second elastic member accommodation groove 12 ($h_1 > h_2$), and when the second elastic member 52 maximally deforms, the second elastic member 52 may fill the entire second elastic member accommodation groove 12, and the height ($h_1$) of the second elastic member 52 and the height ($h_2$) of the second elastic member accommodation groove 12 may be 0 mm $< h_1 - h_2 \leq$ 5 mm, preferably 0.05 mm $< h_1 - h_2 \leq$ 3 mm, and more preferably 0.1 mm $< h_1 - h_2 \leq$ 0.3 mm.

Figure 9:
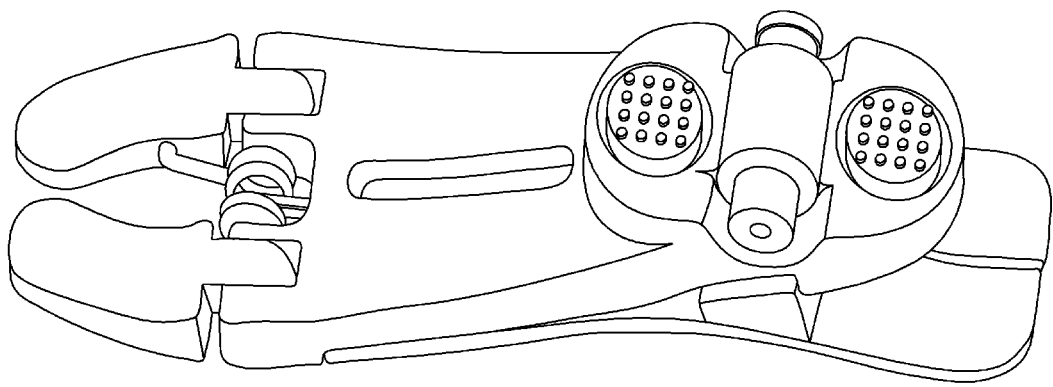
FIG. 9 is an image view showing the state in which an elastic member of an ankle joint has been accommodated in an elastic member seat groove in the artificial foot according to the present invention.

In the present invention, FIG. 9 is an image of the artificial foot 100 with the adapter 40 removed and the second elastic member 52 accommodated in the second elastic member accommodation groove 12. Referring to FIGS. 2 and 9, in the artificial foot 100 according to the present invention, the ankle angle can be limited within the range of $-30° \leq \theta \leq 30°$, preferably $-20° \leq \theta \leq 20°$, and more preferably $-10° \leq \theta \leq 10°$ with respect to a vertical surface in the longitudinal direction of the hinge pin along a front/rear central axis by adjusting the size of the second elastic member accommodation groove 12 and the second elastic member 52.

Since the artificial foot 100 according to the present invention includes the ankle joint 50, the ankle joint and the toes of artificial foot 100 rotate and kick off the ground using the energy obtained by the weight of the wearer on a slope, so there is an effect that it is possible to minimize dragging.

According to an embodiment of the present invention, the artificial foot 100 may include a cushion part 60 on a side of the lower portion of the foot body 11, that is, at a portion corresponding to the heel to be able to absorb a shock that is transmitted from the surface when walking.

The cushion part 60, which is made of an elastic material to make a wearer feel comfort while walking, absorbs a shock generated by contact between the ground and the heel when a wearer walks in the stance phase so that the wearer can stably walk. Further, the cushion part 60 may be made of a non-elastic material. That is, the material is not limited as long as it can stably support a wearer. Further, the cushion rubber 13 is disposed between the foot body 11 and the cushion part 60, so the cushion part 60 can elastically support a load.

As described above, since the artificial foot 100 according to the present invention includes the toe joint 30 and the ankle joint 50, a wearer can the free rotation angle of the ankle joint at the early, middle, and latter stage of the stance phase while walking, and the toes can kick off the ground using the elasticity of the spring at the latter stage of the stance phase.

Although exemplary embodiments of the present invention were described above, the present invention may be changed and modified in various ways by those skilled in the art without departing from the spirit of the present invention described in claims by replacing, changing, or removing the components, which will be included in the scope of the present invention. For example, the components described as single parts may be combined. The scope of the present disclosure is defined by the following claims rather than the above detailed description, and all of changes and modifications obtained from the meaning and range of claims and equivalent concepts should be construed as being included in the scope of the present disclosure.

DESCRIPTION OF THE REFERENCE NUMERALS IN THE DRAWINGS

10: foot body part
11: foot body
12: second elastic member accommodation groove
13: cushion rubber
20: toe part
21: toe member
22: toe connection member connection hole
30: toe joint
31: toe connection member
32: first elastic member
40: adapter
41: adapter body
42: adapter connection member connection hole
43: artificial limb-fastening pyramid
50: ankle joint
51: adapter connection member
52: second elastic member
53: washer, 54: shaft-fixing guide, 55: bolt
60: cushion part

INDUSTRIAL APPLICABILITY

According to the present invention, since the toes of the artificial foot rotate when a wearer walks, when the artificial toes come in contact with the ground, energy is stored due to the load by the weight and the toes kick off the ground as much as the elastic energy accumulated by the spring, so the toe members of the artificial foot do not drag on the ground. Accordingly, the wearer does not need to lift up the hip joints, so the wearer can walk similar to normal walking.

Further, since the ankle joint and the toes of artificial foot rotate and kick off the ground using the energy obtained by the weight of the wearer on a slope, so there is an effect that it is possible to minimize dragging.

The invention claimed is:
1. An artificial foot comprising:
a foot body part;
a toe part rotatably disposed at a first end of the foot body part;
a toe joint connecting the foot body part and the toe part to each other;
an adapter disposed on a top of a second end of the foot body part; and
an ankle joint,
wherein the toe joint includes a toe connection member and a first elastic member,
wherein the ankle joint includes an adaptor connection member and a second elastic member,
wherein the second elastic member is disposed in a second elastic member accommodation groove formed in the foot body part,
wherein the second elastic member and the second elastic member accommodation groove are formed in any one of cylindrical, elliptical cylindrical, and polygonal cylindrical shapes,
a size of a cross-section cut perpendicular to a central axis of the second elastic member is smaller than a size of a cross-section cut perpendicular to a central axis of the second elastic member accommodation groove, a height (h1) of the second elastic member is larger than a height (h2) of the second elastic member accommodation groove (h1>h2), and
when the second elastic member maximally deforms, the second elastic member fills an entirety of the second elastic member accommodation groove, and the height (h1) of the second elastic member and the height (h2) of the second elastic member accommodation groove are 0 mm<h1-h2≤5 mm.

2. The artificial foot of claim 1, wherein the toe joint includes a toe connection member and a first elastic member,
the first elastic member is disposed between the toe part and the foot body part and elastically supports the toe part, and
the toe connection member connects the toe part and the foot body part to each other such that the toe part can rotate.

3. The artificial foot of claim 2, wherein the toe part pivots a rotation angle (theta) on the toe connection member.

4. The artificial foot of claim 3, wherein the rotation angle (θ) of the pivoting θ is 0≤θ≤90°.

5. The artificial foot of claim 3, wherein the toe connection member is a hinge pin.

6. The artificial foot of claim 2, wherein the first elastic member is a torsion spring.

7. The artificial foot of claim 1, wherein the foot body part includes a foot body, the second elastic member accommodation groove, and a cushion rubber.

8. The artificial foot of claim 1, wherein the toe part includes toe members and a toe connection member connection hole.

9. The artificial foot of claim 1, wherein the adapter includes an adapter body, an adapter connection member connection hole, and an artificial limb-fastening pyramid.

10. The artificial foot of claim 1, wherein the ankle joint is disposed between the foot body part and the adapter and rotatably connects the adapter to the foot body part.

11. The artificial foot of claim 1, wherein the second elastic member is made of elastic rubber.

12. The artificial foot of claim 1, wherein the adapter connection member connects the adapter and the foot body part such that the adapter can rotate, and
   the second elastic member is disposed between the adapter and the foot body part and elastically supports the adapter.

13. An artificial foot comprising:
   a foot body part;
   a toe part rotatably disposed at a first end of the foot body part;
   a toe joint connecting the foot body part and the toe part to each other;
   an adapter disposed on a top of a second end of the foot body part; and
   an ankle joint,
   wherein the toe joint includes a toe connection member and a first elastic member,
   wherein the ankle joint includes an adaptor connection member and a second elastic member,
   wherein the second elastic member is disposed in a second elastic member accommodation groove formed in the foot body part,
   wherein the second elastic member and the second elastic member accommodation groove are formed in cylindrical shapes,
   a diameter ($d1$) of a cross-section cut perpendicular to a central axis of the second elastic member is smaller than a diameter ($d2$) of a cross-section cut perpendicular to a central axis of the second elastic member accommodation groove a ($d1<d2$), a height ($h1$) of the second elastic member is be larger than a height ($h2$) of the second elastic member accommodation groove ($h1>h2$), and
   when the second elastic member maximally deforms, the second elastic member fills an entirety of the second elastic member accommodation groove, and the height ($h1$) of the second elastic member and the height ($h2$) of the second elastic member accommodation groove are $0\ mm<h1-h2\leq 5\ mm$.

14. The artificial foot of claim 12, wherein the adapter pivots on the adapter connection member.

15. The artificial foot of claim 14, wherein the adapter connection member is a hinge pin.

* * * * *